United States Patent
Biggs

Patent Number: 5,755,575
Date of Patent: May 26, 1998

[54] DENTAL IMPLANT DELIVERY SYSTEM AND METHOD

[75] Inventor: Michael John Biggs, San Diego, Calif.

[73] Assignee: Sulzer Calcitek, Inc., Carlsbad, Calif.

[21] Appl. No.: 689,696

[22] Filed: Aug. 16, 1996

[51] Int. Cl.⁶ .................................................. A61C 8/00
[52] U.S. Cl. ........................ 433/173; 433/174; 206/63.5
[58] Field of Search .................................... 433/173, 174, 433/172, 175, 176; 206/63.5, 368, 369

[56] References Cited

U.S. PATENT DOCUMENTS

| | | | |
|---|---|---|---|
| 3,990,438 | 11/1976 | Prichard | 606/73 |
| 4,027,392 | 6/1977 | Sawyer et al. | 433/174 |
| 4,259,072 | 3/1981 | Hirabayashi et al. | 433/173 |
| 4,533,942 | 8/1985 | Sutter | 433/225 |
| 4,712,681 | 12/1987 | Branemark et al. | 206/438 |
| 4,713,003 | 12/1987 | Symington et al. | 433/173 |
| 4,763,788 | 8/1988 | Jorneus | 206/438 |
| 4,856,648 | 8/1989 | Krueger | 206/63.5 |
| 5,018,970 | 5/1991 | Stordahl et al. | 433/75 |
| 5,030,095 | 7/1991 | Niznick | 433/173 |
| 5,030,096 | 7/1991 | Hurson et al. | 433/173 |
| 5,035,619 | 7/1991 | Daftary | 433/173 |
| 5,062,800 | 11/1991 | Niznick | 433/229 |
| 5,073,111 | 12/1991 | Daftary | 433/173 |
| 5,145,372 | 9/1992 | Daftary et al. | 433/173 |
| 5,167,664 | 12/1992 | Hodorek | 606/73 |
| 5,282,746 | 2/1994 | Sellers et al. | 433/172 |
| 5,297,963 | 3/1994 | Daftary | 433/172 |
| 5,312,254 | 5/1994 | Rosenlicht | 433/173 |
| 5,362,235 | 11/1994 | Daftary | 433/172 |
| 5,366,374 | 11/1994 | Vlassis | 433/173 |
| 5,368,160 | 11/1994 | Leuschen et al. | 206/339 |
| 5,415,545 | 5/1995 | Shaw | 433/173 |
| 5,431,567 | 7/1995 | Daftary | 433/172 |
| 5,484,285 | 1/1996 | Morgan et al. | 433/173 |
| 5,538,428 | 7/1996 | Staubli | 433/173 |
| 5,582,299 | 12/1996 | Lazzara et al. | 206/63.5 |
| 5,622,500 | 4/1997 | Niznick | 433/173 |

FOREIGN PATENT DOCUMENTS 1727808  4/1982  U.S.S.R.

*Primary Examiner*—John J. Wilson
*Attorney, Agent, or Firm*—Philip S. Lyren

[57] ABSTRACT

A packaging system for dental implants and method for implanting a packaged implant. The packaging system includes a vial and a vial cap forming an enclosure for an implant and driver cap. The driver cap is press fit to both the implant and vial cap and engages the implant to impart driving forces thereto. Once the implant is driven to into position, the driver cap serves as a conventional healing screw to cover the implant.

26 Claims, 5 Drawing Sheets

DENTAL IMPLANT DELIVERY SYSTEM AND METHOD

BACKGROUND OF THE INVENTION

Dental implants are typically packaged and shipped in a package or kit. These packages maintain the implant in a sterile environment and are opened just before the implant is needed during the surgical procedure.

FIGS. 1 and 2 illustrate an example of one such prior art package shown generally at 10. Package 10 includes a threaded implant 12, a driver mount 14, a healing or retaining screw 16, a vial 18, and a vial cap 20. Implant 12 has outer threads 30, a bore 32 to aid osseointegration, and a top portion 34 having an inner threaded chamber 36 to receive screw 16.

Screw 16 secures driver mount 14 to implant 12. In this regard, driver mount 14 has an inner cavity 40 with a ridge 42 and an end 44 adapted to abut top portion 34 of implant 12. Screw 16 includes a head 48 and outer threads 50. Screw 16 is dimensioned to fit within cavity 40 such that the bottom planar surface of head 48 abuts against ridge 42 and threads 50 screw into chamber 36.

Cap 20 has a generally cylindrical outer surface 52 having ridges 53 for hand grasping. A socket section 54 forms a cavity 56 that fits over the outer surface of driver mount 14. This socket section is press fit over the driver mount and provides a removable connection.

Vial 18 has a generally elongated, cylindrical configuration with a closed end 60 and an open end 62. Open end 62 receives cap 20 and abuts against the outer surface of socket section 54 to provide a removable connection. Vial 18 supports cap 20 and provides a protective, sealed enclosure for implant 12.

In order to install implant 12 into the patient's jawbone, an implant site is prepared using conventional surgical procedures. Typically, an incision is made along the gingival tissue at the implant site, a cylindrical bore is drilled into the alveolar bone, and the bore is tapped. Once the site is fully prepared, vial 18 is separated from cap 20, and the accompanying implant is positioned above the implant site. The end of the implant is fit within the bore, and the cap is then gently twisted with finger pressure to thread the implant. The implant is threaded until the resistive torque becomes great enough so cap 20 twists off driver mount 14. The cap is then removed from the driver mount, and the implant is further screwed to fully sit within the bore.

In this regard, driver mount 14 includes an engaging means (not shown) for engaging a rachet or other driving tool.

Once the implant is completely positioned within the implant site, screw 16 is removed. The screw includes a cavity 66 for receiving and engaging a wrench or other tool. When the screw is disengaged from the implant, driver mount 14 is then removed from contact with the implant. The screw is then re-engaged with the implant. In this position, the screw functions as a conventional healing screw and covers and protects the top of the implant. The gingival tissue is then sutured and the implant remains within the bone for several months as osseointegration and healing occur. During the second surgical procedure, the implant is re-exposed and the screw is removed. Thereafter, an abutment is affixed onto the top of the implant and a dental prosthesis is affixed to the abutment.

One disadvantage associated with dental implant procedures is that many steps are required during the surgical implantation procedure. Any additional or unnecessary steps make the surgical procedure more lengthy and cumbersome and may ultimately increase the risk and trauma to the patient. In this regard, once the implant is positioned in the implant site, the surgeon must obtain a wrench or other tool to manually engage and completely remove the screw from the implant. The driver mount must then be carefully removed. Next, the surgeon must use the wrench or tool to reengage the screw and screw it back into the implant.

A further disadvantage associated with dental implant procedures is that once the implant is correctly positioned within the jawbone, movement and disturbance of the implant should be minimal. In this regard, the implant must be carefully positioned and oriented to the correct position. As noted though, in present implant procedures, the screw is completely removed and then replaced in order to separate the driver mount from the implant. The torque and related forces required to disengage and then re-engage the screw imparts to the implant as well. These forces disturb the seating or position of the implant and may cause it to rotate, loosen, or otherwise move.

As another disadvantage, it is desirable to minimize the amount of handling of the packaging system components. The surgeon or clinician may drop the retaining screw, vial cap, implant, or driver mount. If these components are dropped outside the oral cavity, they may be lost or contaminated; and if dropped inside the oral cavity, they could be swallowed or aspirated.

As yet another disadvantage, implant packages require a separate driver mount generally held to the implant with a retaining screw. The driver mount is used to drive or screw the implant into the bore in the alveolar bone. Typically, a wrench or other driving tool is used to engage the driver mount. Elimination of the driver mount would reduce the overall number of separate components in the implant package. Additionally, a separate driver tool would not be needed. The overall cost of the implant package would decrease and the packaging efficiency would increase.

As yet another disadvantage, healing screws are not utilized to drive the implant into the bone. These screws are typically used to retain the driver mount to the implant or to provide a protective cap for the implant.

It therefore would be advantageous to employ a dental implant package requiring a fewer number of steps during the surgical implantation procedure. A surgical procedure requiring fewer steps ultimately would be less traumatic on the patient, more expeditiously performed, and less burdensome on the surgeon, to name a few examples.

It also would be desirable to provide a dental implant package and corresponding implant procedure that would more fully minimize movement and disturbance of the implant after it is correctly positioned within the jawbone. Further, the torque and related forces required to disengage the screw from the implant should be minimized.

Additionally, it would be desirable to provide a dental implant package and implant procedure that minimizes the amount of handling of the packaging system components.

It also would be desirable to provide an implant package that did not require a separate driver mount. Elimination of the driver mount reduces the number of separate components required in the implant package and additionally eliminates the need for a separate driver tool. Such a dental implant package would be less expensive to manufacture, more efficient to utilize, and eliminate the extra step of removing the driver mount during the implant procedure.

It also would be advantageous to provide a healing screw that may be employed to drive the implant into the bore of the alveolar bone. Such a healing screw would not only serve as a protective cap for the implant, but also serve to drive the implant into the bone.

It therefore would be desirable to provide a dental package system that eliminates the need for a separate driver mount. Such a system would have a fewer number of overall components and thus be less expensive to manufacture and reduce the risk of dropping a component during the implant procedure or touching a component and jeopardizing its sterility. Additionally, such a delivery system would decrease the overall number of surgical steps and thus provide an easier and more efficient surgical procedure. The elimination of the added driver mount would also eliminate a separate counter torque or driving tool and any additional steps during surgery for removing the driver mount and corresponding screw. The present invention fulfills these needs and provides further advantages.

SUMMARY OF THE INVENTION

The present invention is directed toward a dental implant package or dental implant delivery system that allows for direct placement of a dental implant into the osteotomy site without touching or otherwise jeopardizing the sterility of the implant body. The delivery system includes a vial and a vial cap that form a protective enclosure for an implant and a driver cap. The driver cap has a head portion removably connected to the vial and an extension portion removably connected to the implant.

During an implant procedure, the vial is separated from the vial cap and attached driver cap and implant. While holding the vial cap, the implant is then partially positioned into the implant site, and the vial cap is gently twisted with finger pressure to thread the implant partially into the bone. After a predetermined amount of resistive torque, the vial cap then disengages from the head portion of the driver cap. This head portion includes an engagement for receiving a driving tool. The driving tool engages with the driver cap engagement and the implant is driven or screwed to the desired depth and location.

The delivery system of the present invention is particularly advantageous because the number of steps during the dental implant procedure are minimized. In this regard, no steps are required to remove a separate driver mount or like component. Once the vial cap is disengaged from the driver cap, the driver cap is used to impart torque to insert the implant. Thereafter, no additional removal steps are required since the driver cap then functions as a conventional healing cap to cover the top of the implant.

As another advantage, once the implant is driven to the desired location, no component needs to be removed from the implant. As such, movement and disturbance of the implant is minimized. In this regard, once the implant is driven to the correct position and orientation, the driver cap then serves as the noted healing cap. This driver cap need not be removed until sometime later when the dental prosthesis is ready to be attached to the implant.

As yet another advantage, the implant procedure minimizes the amount of handling or contact with the packaging system components. As such, the likelihood that a component may be dropped, mishandled, contaminated, or otherwise misplaced is greatly reduced.

As yet another advantage, the delivery system of the present invention does not require a separate driver mount or like component. Instead, the driver cap of the present invention serves multiple functions. First, the driver cap retains the implant within the vial and additionally connects it to the vial cap. Second, the driver cap is used as a driving tool to impart torque or a driving force to the implant to position it within the jawbone. Third, the driving cap serves as a conventional healing cap.

The invention, accordingly, comprises the apparatus and method possessing the construction, combination of elements, and arrangement of parts which are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENTS

Figures 3, 4:
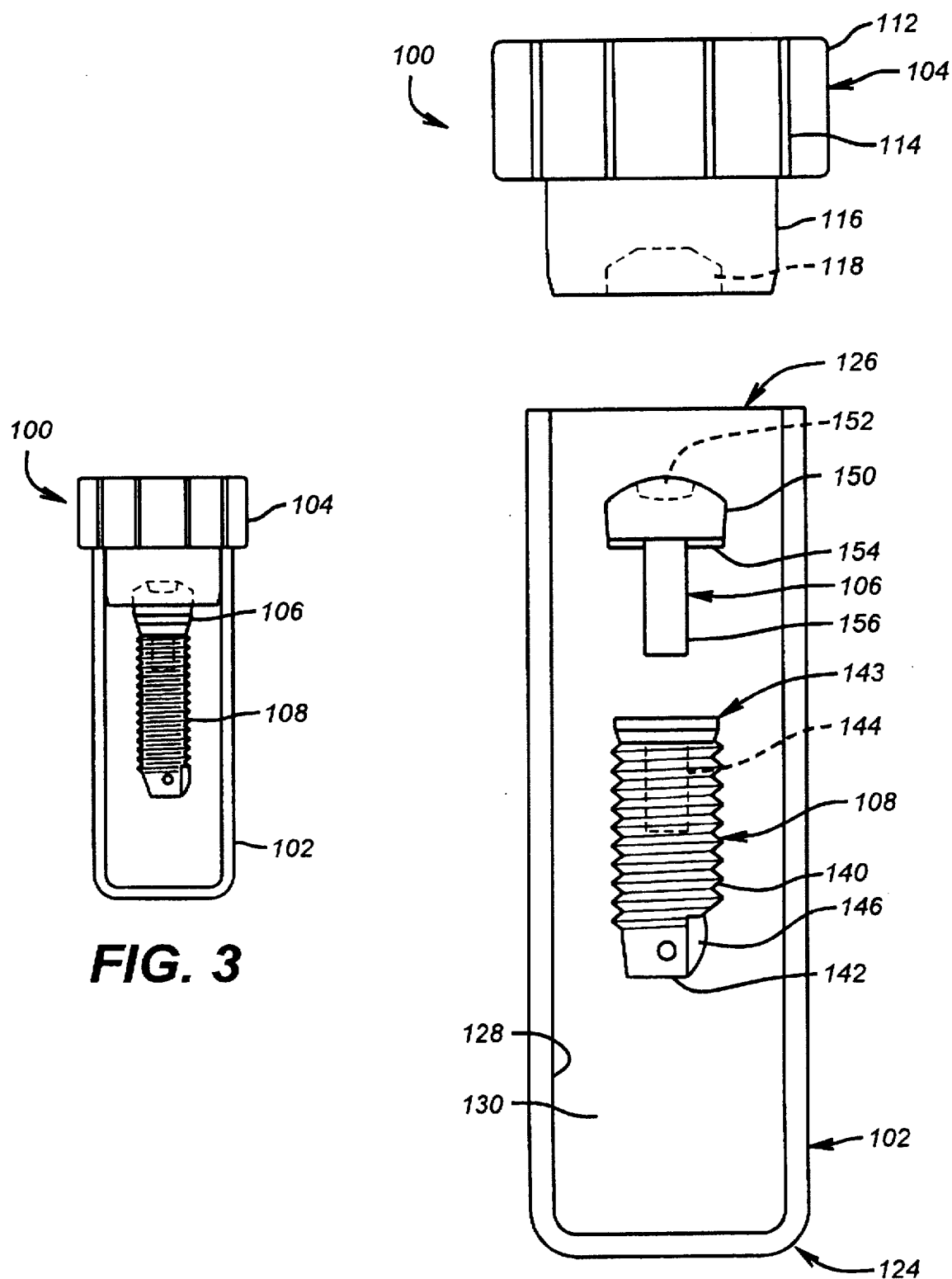
FIG. 3 is a plan view of a dental delivery system of the present invention.
FIG. 4 is an exploded plan view of the dental delivery system of FIG. 3.

FIGS. 3 and 4 illustrate a dental delivery system generally at 100. System 100 includes a vial 102, a vial cap 104, a driver cap 106, and an implant 108. Together, vial 102 and vial cap 104 form a protective enclosure for driver cap 106 and implant 108. This enclosure maintains the implant and driver cap in a sealed and sterile environment.

Vial cap 104 preferably has a cylindrical configuration with a top portion 112 having a plurality of parallel ridges 114. Top portion 112 is configured to be hand grasped and ridges 114 provide a more firm gripping outer surface. Vial cap 104 includes an extension 116 having an inner cavity 118 (shown with dashed lines).

Figure 1:
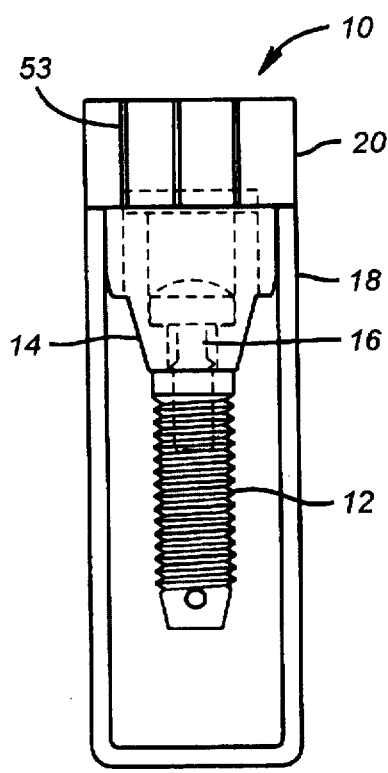
FIG. 1 is a plan view of a prior art dental delivery system.
Figure 2:
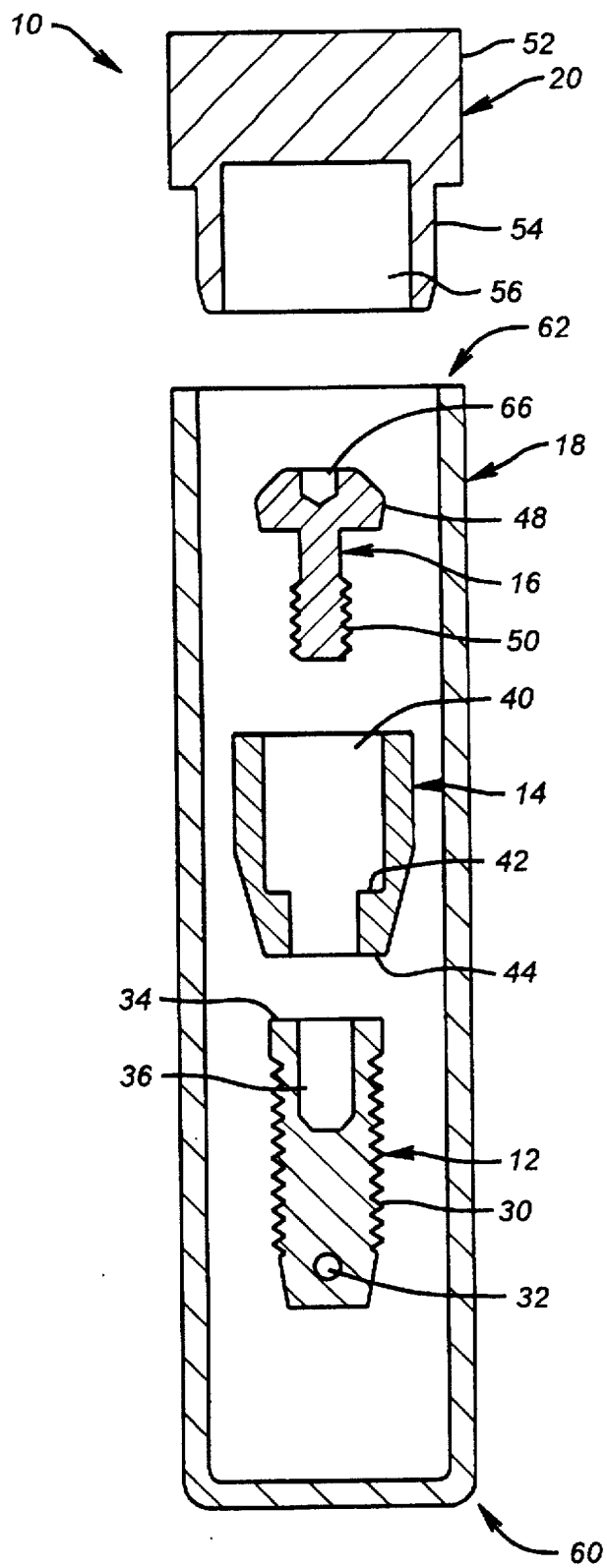
FIG. 2 is a cross section of an exploded plan view of the dental delivery system of FIG. 1.

Vial 102 has an elongated cylindrical configuration with a closed end 124 and an oppositely disposed opened end 126. Vial cap 104 is removably connectable to vial 102 and forms a complete enclosure when engaged with opened end 126, as best shown in FIG. 1. Preferably, extension 116 of vial cap 104 press fits into vial 102 to form a seal. As shown, vial 102 has an inner surface 128 that defines an inner cavity 130. Extension 116 fits within cavity 130 to abut against inner surface 128.

It should be noted that vial cap 104 and vial 102 are removably connectable and form the noted enclosure for implant 108 and driver cap 106. It will be appreciated that vial cap 104 and vial 102 may have various designs and configurations known or obvious to those skilled in the art in order to form the requisite enclosure and housing for the implant and driver cap.

Implant 108 may be any one of various implants known to those skilled in the art. For illustration purposes, implant 108 has outer threads 140, a bore 142 to aid osseointegration, a top portion 143, an inner chamber 144 to receive driver cap 106, and a tapping channel 146.

Driver cap 106 has a head portion 150, an engagement 152, a contact driver 154, and an extension 156. As one important advantage, driver cap 106 is removably connectable to both implant 108 and vial cap 104. In this regard, extension 156 is configured to be press fit into and engageable with inner chamber 144 of implant 108. Likewise, head 150 is configured to be press fit into and engageable with cavity 118 of vial cap 104.

Figure 5:
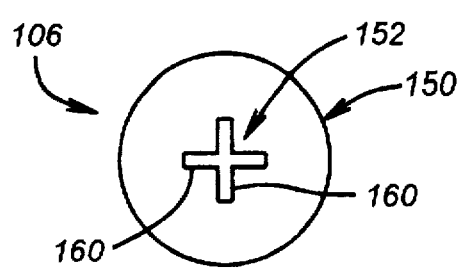
FIG. 5 is a top view of a driver cap.

Engagement 152 of driver cap 106 preferably is configured to receive and engage a driver, torquing tool, or the like. FIG. 5 shows a top view of head 150 and illustrates an example of one such engagement 152. Two cross slots 160 are provided to engage a driving tool. It will be appreciated that cross slots 160 represent one example of an engagement for engaging various driving tools, and other engagements are known to those skilled in the art and useable with the present invention.

Figure 6:
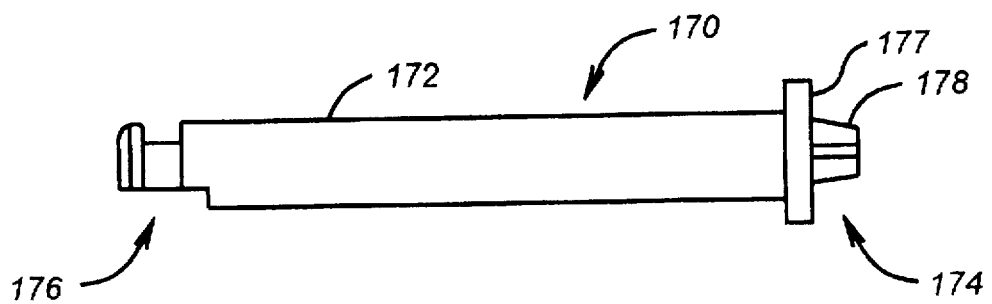
FIG. 6 is a plan view of a driver.

Turning now to FIG. 6 a driver is shown generally at 170. Driver 170 has an elongated shaft portion 172 and two oppositely disposed ends 174 and 176. End 176 has a standard right-angle latchlock shank interface to receive a dental tool (not shown) for driving. This dental tool, for example, may be a handle for manual driving or a motorized drill for automatic driving. End 174 has an abutting surface 177 and a cross slot extension 178. Extension 178 is configured to engage cross slots 160 of FIG. 5. End 174 may be provided with various configurations known to those skilled in the art in order to engage head 150 and engagement 152.

Figure 7:
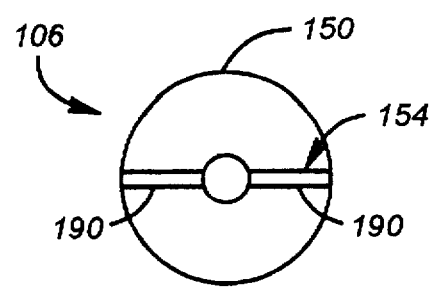
FIG. 7 is a bottom view of the driver cap of FIG. 5.

Contact driver 154 of driver cap 106 engages implant 108 in order to drive or screw the implant. FIG. 7 shows a bottom view of driver cap 106 and illustrates one example of contact driver 154. Two wings 190 extend downwardly from head 150. These wings are configured to engage top portion 143 of implant 108 (FIG. 4) and impart torque and drive forces thereto.

Figure 8:
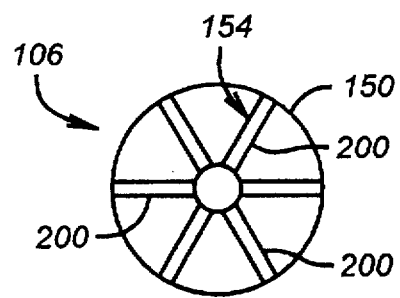
FIG. 8 is a bottom view of an alternate embodiment of the driver cap of FIG. 5.

FIG. 8 illustrates another example of contact driver 154. As shown, a plurality of wings 200 extend downwardly from head 150. These wings are configured to engage top portion 143 of implant 108 (FIG. 4) and impart torque and drive forces thereto.

Figure 9:
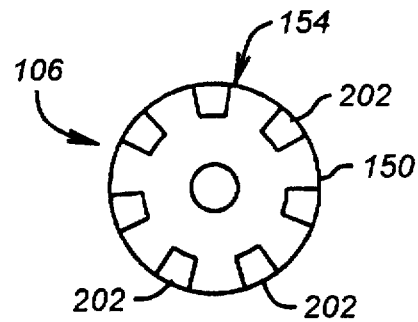
FIG. 9 is a bottom view of another alternate embodiment of the driver cap of FIG. 5.

FIG. 9 illustrates another example of contact driver 154. As shown, a plurality of splines 202 extend downwardly from head 150. These splines are configured to engage top portion 143 of implant 108 (FIG. 4) and impart torque and drive forces thereto.

Figure 10:
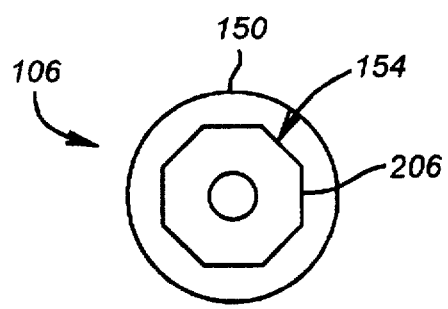
FIG. 10 is a bottom view of another alternate embodiment of the driver cap of FIG. 5.

FIG. 10 illustrates another example of contact driver 154. As shown, a hexagonal configuration 206 exist about the bottom portion of head 150. This configuration is configured to engage top portion 143 of implant 108 (FIG. 4) and impart torque and drive forces thereto. It will be appreciated that although a hexagonal configuration is shown, other geometries, such as square, also are employable and are known to those skilled in the art.

It will be appreciated that contact driver 154 of driver cap 106 may have various structural configurations. It is important that the driver cap is able to impart torque or driving forces to the implant. FIGS. 7–10 show examples of contact drivers utilizable for engaging and driving the implant.

One important advantage of the present invention is that the overall number of steps required during a dental implant procedure are minimized. Reference should be made to FIGS. 3 and 4 for the following discourse. In order to install implant 108 into the alveolar bone of the patient, an implant site may be initially prepared using conventional surgical procedures. Once the site is prepared and ready to receive the implant, vial 102 is separated from vial cap 104; and the accompanying implant 108 and driver cap 106 are positioned above the implant site. Vial cap 104 is then gently twisted with finger pressure around top portion 112 to thread or insert implant 108 into the bone. The implant is threaded or driven until the resistive torque becomes great enough so vial cap 104 disengages from driver cap 106. At this time, implant 108 remains partially implanted within the bone, and vial cap 104 may be discarded. The implant is then further screwed or driven to the desired position within the implant site. In this regard, end 174 of driver 170 (FIG. 6) engages with engagement 152 of driver cap 106. Torque or driving force imparts from end 174 to engagement 152 and then to contact driver 154. Contact driver 154, in turn, imparts this torque or driving force to top portion 143 of implant 108. Once the implant is driven to its desired position and orientation, end 174 of driver 170 disengages from engagement 152.

As another important advantage of the present invention, driver cap 106 performs multiple functions and tasks during the implant procedure. In this regard, while implant 108 is being driven or screwed into its desired position, driver cap 106 functions as a driver. In particular, the contact driver transfers torque and driving forces from the driving tool to the implant. Then, once the implant is completely and correctly positioned within the implant site, driver cap 106 functions as a conventional healing cap or screw. In this regard, extension 156 remains engaged within inner chamber 144 and head 150 remains in abutment with top portion 143 of implant 108. In this position, driver cap 106 covers and protects implant 108. The implant site is then closed in a conventional manner, and implant 108 and driver cap 106 remain within the bone for several months as osseointegration and healing occur.

During a subsequent surgical procedure, implant 108 and driver cap 106 are re-exposed. Thereafter, extension 156 dislodges and disengages from inner chamber 144 and driver cap 106 is removed from implant 108. Driver cap 106 may then be discarded. Dental prosthesis may then be affixed to the implant in a desired and conventional manner.

Figure 11:
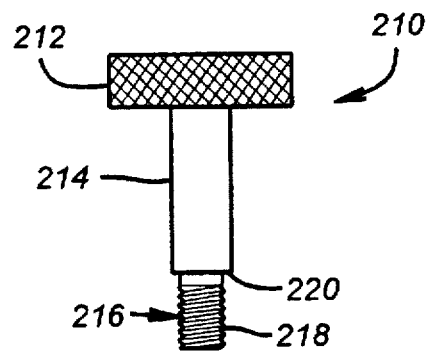
FIG. 11 is a plan view of a removal tool.

FIG. 11 illustrates a removal tool 210 used to remove or disengage driver cap 106 from implant 108. Tool 210 includes a head portion 212 having a knurled outer surface to facilitate hand grasping, a shaft or extension 214 extending downwardly from head 212, and an engagement end 216. In order to remove driver cap 106 from implant 108, engagement end 216 engages head 150 and driver cap 106 is pulled or otherwise removed from implant 108. In this regard, engagement end 216 may, for example, include a threaded portion 218. Threaded portion 218 may be threaded or tapped into head 150 until an edge 220 of shaft 214 abuts against head 150. In this position, engagement end 216 is firmly secured to head 150, and head portion 212 may thereafter be grasped to pull or dislodge extension 156 from inner chamber 144. Thereafter, threaded end 216 may be unscrewed or dislodged from head 150 and driver cap 106 discarded.

Removal tool 210 may have any one of various designs and configurations that would be known or obvious to one skilled in the art. It is important that removal tool 210 be able to engage and remove or dislodge driver cap 106 from implant 108.

Figure 12:
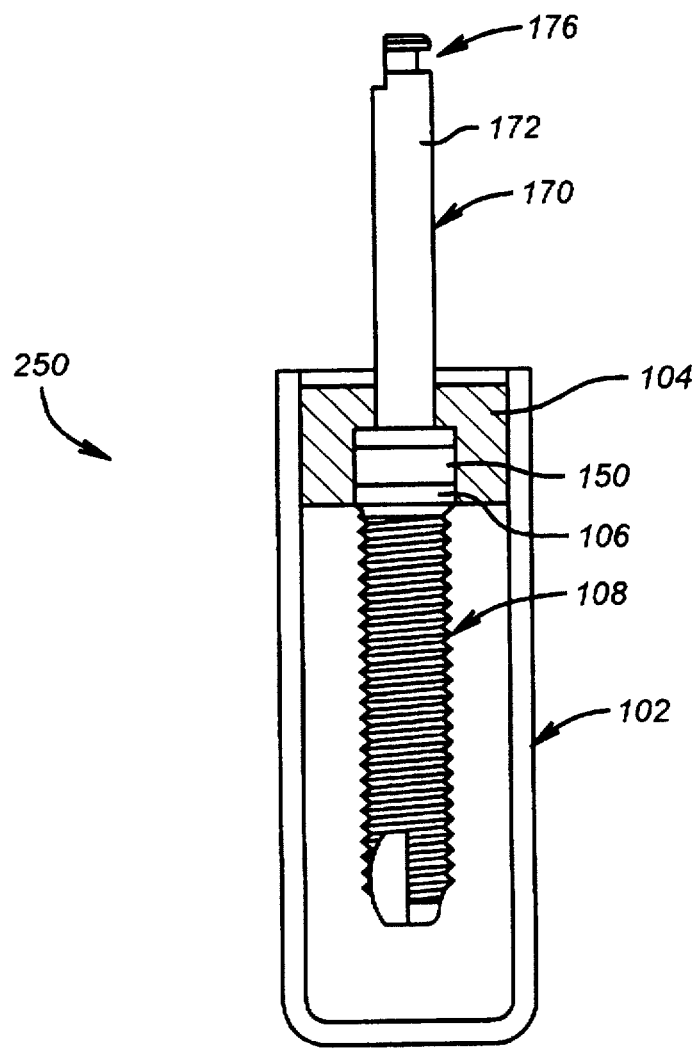
FIG. 12 is a partial cross section plan view of an alternate dental delivery system.
Figure 13:
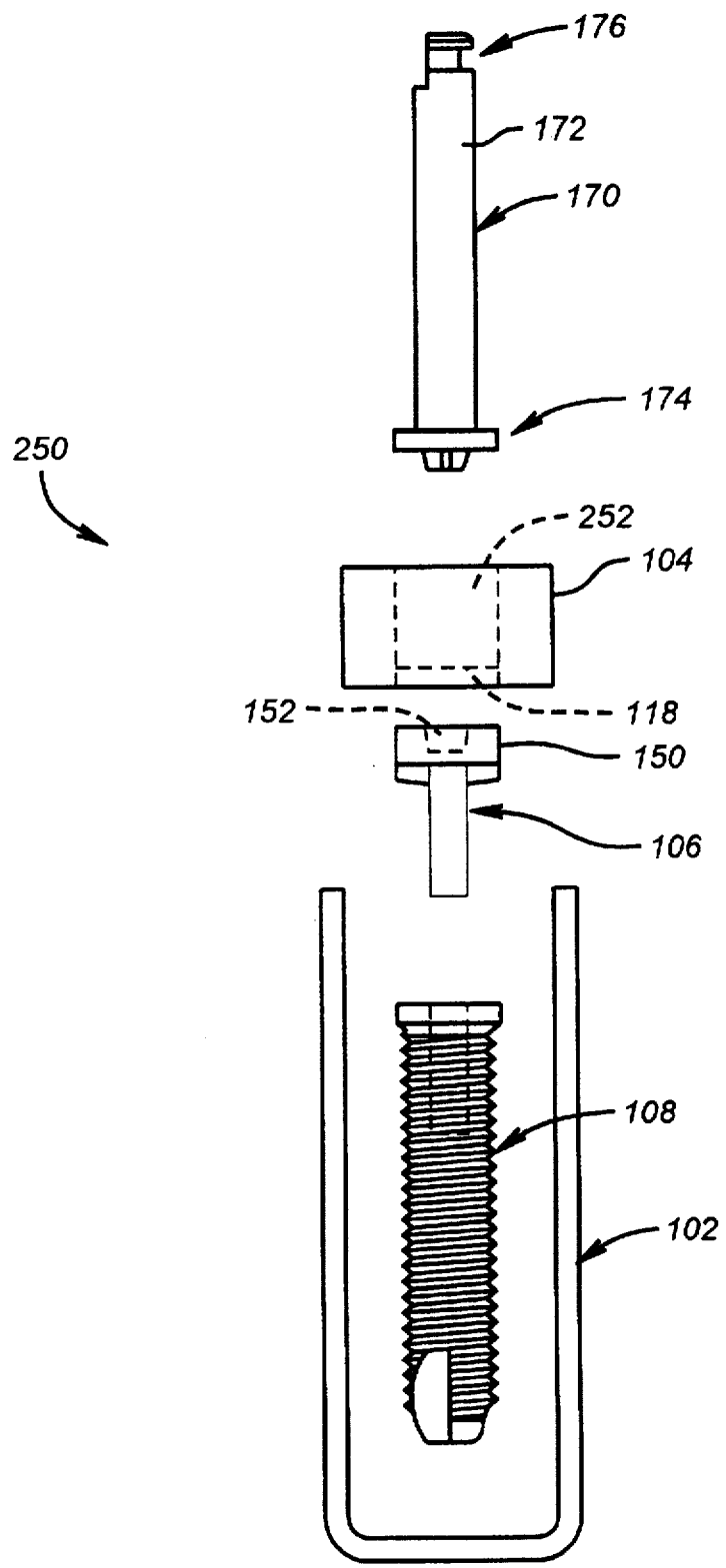
FIG. 13 is an exploded plan view of the dental delivery system of FIG. 12.

FIGS. 12 and 13 illustrate an alternate delivery system 250 to the delivery system 100 shown in FIGS. 3 and 4. For convenience, like numerals designate components common to both delivery systems. As shown then, delivery system 250 includes the addition of driver 170. Driver 170 is removably connectable to the delivery system. In this regard, vial cap 104 includes the addition of an inner cavity 252 (shown with a dashed line) that is adjacent to cavity 118 (shown with a dashed line). This cavity 252 is configured to receive end 174 of driver 170. As shown in FIGS. 6 and 12, end 174 is tapered to press fit into head 150 to retain and hold driver cap 106 during placement of the implant. As shown, end 174 abuts against driver cap 106 such that cross slot extension 178 fits into and engages engagement 152.

Preferably, vial cap 104 is perforated such that it may split and break away from driver 170 and driver cap 106. During removal of vial cap 104 from vial 102, a force is exerted at the perforation which causes a split or tear to occur along the perforation. Therefore, the press fit between driver 170 and driver cap 106 is sufficient to maintain them connected.

Delivery system 250 is particularly advantageous since the surgeon performing the implant operation need only contact shaft 172 and end 176 of driver 170 in order to completely install implant 108 within the implant site. As such, the sterile integrity of implant 108 and driver cap 106 are maintained. As an additional advantage, since vial cap 104 splits away when removed from vial 102 and since driver 170 is preattached to driver cap 106, the implant can be delivered to the implant site in one motion without the added step of removing the vial cap.

In order to install implant 108 into the patient's bone, an implant site is prepared using conventional surgical procedures. Once the site is prepared, the surgeon may grasp vial 102 and insert end 176 into a dental tool (not shown) used for manual driving or electronic driving. Driver 170, vial cap 104, driver cap 106, and implant 108 are then removed from vial cap 102. At this point, vial cap 104 splits and automatically breaks away and separates from driver 170. Implant 108 is then positioned above the implant site. Driver 170 is then used to torque, drive, or screw, implant 108 into the desired positioned in the patient's bone. As noted herein, the driving force is imparted from end 174 to engagement 152 and then from driver cap 106 to implant 108.

Once implant 108 is in the correct position and orientation, driver 170 is disengaged from driver cap 106. The amount of force needed to disengage driver 170 from engagement 152 will not cause driver cap 106 to disengage from implant 108. The implant site is then closed using conventional techniques. During a subsequent surgical procedure, driver cap 106 is removed from implant 108 using removal tool 210 (FIG. 10) as described herein.

Since certain changes may be made in the above-described apparatus and method without departing from the scope of the invention herein involved, all matter contained in the description or shown in the accompanying drawings shall be interpreted as illustrative and not in a limiting sense.

The invention claimed is:

1. A delivery system for implanting a dental implant into an implant site, comprising:
   a vial;
   a vial cap for closing said vial; and
   a driver cap removably connectable to said vial cap and to said implant, and including a head portion and a contact drive extending outwardly from said head portion for engaging and driving said implant into said implant site.

2. The packaging system of claim 1 in which said vial cap includes a cavity that engages said head portion to hold said driver cap.

3. The packaging system of claim 1 in which said contact drive extends downwardly from said head portion and engages said implant.

4. The packaging system of claim 1 in which said contact drive transfers rotational driving forces to said implant.

5. The packaging system of claim 1 in which said head portion has an engagement portion oppositely disposed from said contact drive, wherein said engagement portion receives a driving force and said contact drive transfers said driving force to said implant.

6. The packaging system of claim 1 further comprising a driving tool that connects to said vial cap and is engageable with said driver cap.

7. The packaging system of claim 6 in which:
   said driver cap includes a cavity for receiving said driving tool;
   said vial cap includes a cavity for holding said driving tool; and
   said driving tool imparts a driving force to said cavity in said driver cap, and said contact drive imparts said driving force to said implant.

8. A method for implanting a dental implant within an implant site, comprising the steps of:
   providing an implant delivery system having a vial, a vial cap for enclosing said vial, a driver cap connected to said vial cap, and a dental implant connected to said driver cap;
   removing said vial from said vial cap, said implant, and said driver cap;
   grasping said vial cap to position said implant at said implant site;
   rotating said vial cap to partially drive said implant into said implant site and to separate said vial cap from said driver cap;
   removing said vial cap from said driver cap; and
   rotating said driver cap to impart a driving force to said implant and drive said implant into said implant site.

9. The method of claim 8 further comprising the steps of:
   providing a driving tool connected at one end to said vial cap and to said driver cap; and
   rotating said driving tool to perform said step of rotating said driver cap, wherein rotation of said driving tool imparts a driving force from said driving tool to said driver cap.

10. The method of claim 9, further comprising the steps of:
    providing said driver cap with an engagement and a contact driver;
    imparting said driving force from said driving tool to said engagement; and
    imparting said driving force from said contact driver to said implant.

11. The method of claim 8 in which said step of rotating said vial cap imparts a driving force from said vial cap directly to said driver cap and then from said driver cap directly to said implant.

12. The method of claim 8 further comprising the steps of:
    engaging a removal tool with said driver cap; and
    sliding said driver cap out of engagement with said implant.

13. The method of claim 12 further comprising the step of pulling said removal tool away from said implant in order to perform said step of sliding said driver cap.

14. The method of claim 8 further comprising the step of retaining said driver cap connected to said implant after said implant is completely driven into said implant site.

15. The method of claim 8 further comprising the step of using said driver cap as a healing screw for said implant.

16. A delivery system for implanting a dental implant into an implant site, comprising:
   a vial;
   a vial cap for closing said vial;
   a healing cap having a head portion, an extension extending from said head portion, and a contact driver engageable with said implant for transferring a driving force to said implant.

17. The delivery system of claim 16 in which:
   said vial cap has an inner cavity; and
   said healing cap has a cylindrical extension that engages said implant and a head portion that engages said inner cavity.

18. The delivery system of claim 16 in which said contact driver engages said implant such that rotational driving forces imparted to said healing cap transfers from said contact driver to said implant.

19. The delivery system of claim 16 in which:
   said vial cap includes a head portion having an extension extending downwardly therefrom;
   said implant includes a top portion; and
   said contact driver has a first end that press fits into said extension and a second end that press fits into said top portion.

20. The delivery system of claim 16 further comprising a driving tool having a first end connected with said vial cap.

21. The delivery system of claim 20 in which:
   said vial cap includes a head portion;
   said first end is connected with said head portion; and
   said first end is removable from said head portion and engageable with said contact driver for driving said implant into said implant site.

22. A healing cap for use with a dental implant, said healing cap comprising:
   a head portion;
   an extension extending outwardly from said head portion; and
   a contact driver at said head portion and engageable with said implant for transferring a rotational driving force to said implant.

23. The healing cap of claim 22 in which said contact driver includes at least one wing extending outwardly from said head portion for engaging said implant.

24. The healing cap of claim 22 in which said contact driver comprises a hexagonal engagement.

25. The healing cap of claim 22 in which said head portion includes an engagement for engaging with a driving tool, wherein said driving tool imparts said rotational driving force to said head and then to said contact driver.

26. The healing cap of claim 22 in which:
   said extension is removably press fit into said implant; and
   said contact driver is removably connectable with said implant.

* * * * *